US008923961B2

(12) United States Patent
Singh et al.

(10) Patent No.: US 8,923,961 B2

(45) Date of Patent: Dec. 30, 2014

(54) ELECTRODE ASSEMBLY FOR DELIVERING A THERAPEUTIC AGENT INTO OCULAR TISSUE

(75) Inventors: Rishi P. Singh, Shaker Heights, OH (US); William G. Lionetta, Harwich Port, MA (US); Marc E. Larosee, Wilmington, MA (US); George R. Watchko, Stoneham, MA (US); John Wrisley, Londonderry, NH (US); Steven L. Thornton, Windham, NH (US); Lawrence R. Moschini, Carlisle, MA (US); David P. Hill, Medfield, MA (US); Michael H. Bunyan, Chelmsford, MA (US); Chi Hang Wu, Quincy, MA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 901 days.

(21) Appl. No.: 13/107,582

(22) Filed: May 13, 2011

(65) Prior Publication Data

US 2011/0275981 A1 Nov. 10, 2011

Related U.S. Application Data

(63) Continuation-in-part of application No. 12/567,653, filed on Sep. 25, 2009, now Pat. No. 8,311,624, and a (Continued)

(51) Int. Cl.
*A61N 1/30* (2006.01)

(Continued)

(58) Field of Classification Search
CPC ......... A61N 1/30; A61N 1/044; A61N 1/325; A61N 1/36046
USPC .......................................................... 604/20
See application file for complete search history.

(56) References Cited

U.S. PATENT DOCUMENTS

| | | | |
|---|---|---|---|
| 2,525,381 | A | 10/1950 | Tower |
| 2,653,516 | A | 9/1953 | Johnson |

(Continued)

FOREIGN PATENT DOCUMENTS

| | | | |
|---|---|---|---|
| WO | WO-02/055058 | A2 | 7/2002 |
| WO | WO-02/058787 | A1 | 8/2002 |

(Continued)

OTHER PUBLICATIONS

Vomaris Wound Care, Inc., "Cell Migration Enhanced with Procellera® Wireless Microcurrent Generating Wound Dressing", PR Newswire, Mar. 4, 2014, pp. 1-2.

(Continued)

*Primary Examiner* — Aarti B Berdichevsky
(74) *Attorney, Agent, or Firm* — Tarolli, Sunheim, Covell & Tummino LLP

(57) ABSTRACT

A contact electrode assembly for delivering at least one therapeutic agent into ocular tissue of a subject includes a flexible dielectric layer, a first electrode portion, and a second electrode portion. The flexible dielectric includes oppositely disposed first and second surfaces. The first electrode portion is disposed on the first surface of the dielectric layer. The second electrode portion is disposed on a portion of the second surface of the dielectric layer. The second electrode portion includes an interdigitated electrode having a first comb-shaped portion defining a first plurality of fingers and a second comb-shaped portion defining a second plurality of fingers. Each of the first electrode portion, the first comb-shaped portion, and the second comb-shaped portion is electrically connectable to a signal source.

10 Claims, 7 Drawing Sheets

Related U.S. Application Data continuation-in-part of application No. 11/874,859, filed on Oct. 18, 2007.

(60) Provisional application No. 61/334,607, filed on May 14, 2010, provisional application No. 61/100,464, filed on Sep. 26, 2008, provisional application No. 60/829,978, filed on Oct. 18, 2006.

(51) Int. Cl.

| | |
|---|---|
| ***A61N 1/32*** | (2006.01) |
| ***A61B 17/02*** | (2006.01) |
| ***G02B 26/00*** | (2006.01) |
| ***A61N 1/04*** | (2006.01) |
| *A61F 9/00* | (2006.01) |

(52) U.S. Cl.

CPC ............ *A61B 17/0231* (2013.01); *A61N 1/325* (2013.01); *A61N 1/303* (2013.01); *A61N 1/306* (2013.01); *A61F 9/0017* (2013.01); *G02B 26/004* (2013.01); *A61N 1/044* (2013.01)

USPC ........................................................... 604/20

(56) References Cited

U.S. PATENT DOCUMENTS

| | | | |
|---|---|---|---|
| 5,246,003 | A | 9/1993 | DeLonzor |
| 5,678,544 | A | 10/1997 | DeLonzor et al. |
| 5,985,316 | A | 11/1999 | Gyory et al. |
| 6,009,345 | A | 12/1999 | Hofmann |
| 6,154,671 | A | 11/2000 | Parel et al. |
| 6,319,240 | B1 | 11/2001 | Beck |
| 6,512,950 | B2 | 1/2003 | Li et al. |
| 6,553,255 | B1 | 4/2003 | Miller et al. |
| 6,670,038 | B2 | 12/2003 | Sun et al. |
| 6,929,949 | B1 | 8/2005 | Hoff et al. |
| 7,137,975 | B2 | 11/2006 | Miller et al. |
| 7,321,795 | B2 | 1/2008 | Bogdanowicz |
| 7,346,389 | B1 | 3/2008 | Newsome |
| 2002/0010414 | A1 | 1/2002 | Coston et al. |
| 2002/0099320 | A1 | 7/2002 | Beck |
| 2004/0176803 | A1 | 9/2004 | Whelan et al. |
| 2005/0148996 | A1 | 7/2005 | Sun et al. |
| 2005/0181018 | A1 | 8/2005 | Peyman |
| 2005/0273046 | A1 | 12/2005 | Kwiatkowski et al. |
| 2007/0082841 | A1 | 4/2007 | Higuchi et al. |
| 2007/0123814 | A1 | 5/2007 | Roy |
| 2007/0260171 | A1 | 11/2007 | Higuchi et al. |
| 2007/0299386 | A1 | 12/2007 | Peyman |
| 2007/0299420 | A1 | 12/2007 | Peyman |
| 2008/0009471 | A1 | 1/2008 | Higuchi et al. |
| 2008/0039792 | A1 | 2/2008 | Meng et al. |
| 2008/0146986 | A1 | 6/2008 | Riga et al. |
| 2009/0312689 | A1 | 12/2009 | Droitcour et al. |
| 2010/0137780 | A1 | 6/2010 | Singh et al. |

FOREIGN PATENT DOCUMENTS

| | | | |
|---|---|---|---|
| WO | WO-2008/063338 | A2 | 5/2008 |
| WO | WO 2011/143596 | A2 | 11/2011 |

OTHER PUBLICATIONS

PCT International Search Report and Written Opinion, dated Jul. 31, 2012, pp. 1-13.

Bejjani et al., “Electrically Assisted Ocular Gene Therapy”, *Survey of Opthalmology*, 52:196-208 (2007) (Abstract Only).

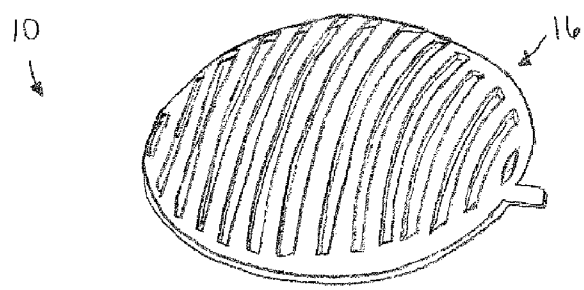
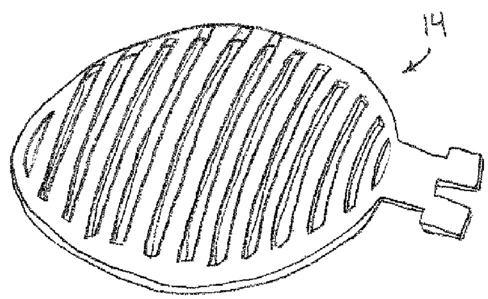
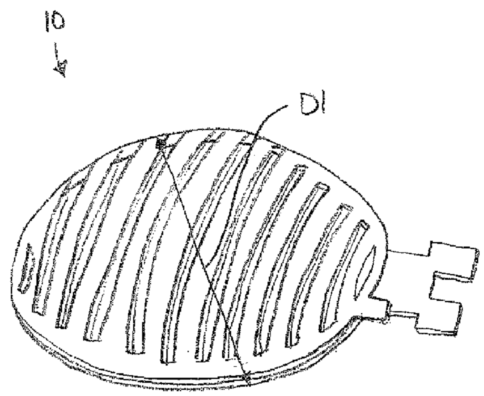
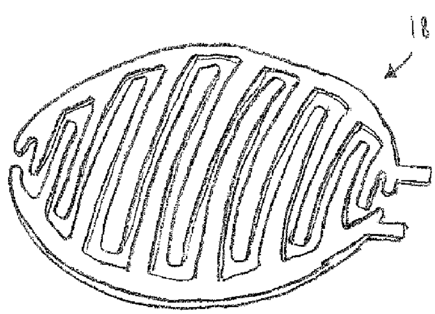
Fig. 1B
Fig. 1A 12
70
74
78
84
80
76
82
D5
72
90
86
88
D6
92

10
16
28
42

12
70
28
42
10

ELECTRODE ASSEMBLY FOR DELIVERING A THERAPEUTIC AGENT INTO OCULAR TISSUE

RELATED APPLICATIONS

This application claims priority from U.S. Provisional Patent Application Ser. No. 61/334,607, filed May 14, 2010 and is a continuation-in-part of U.S. patent application Ser. No. 12/567,653, filed Sep. 25, 2009, which claims priority from U.S. Provisional Patent Application Ser. No. 61/100,464, filed Sep. 26, 2008, and is a continuation-in-part of U.S. patent application Ser. No. 11/874,859, filed Oct. 18, 2007, which claims priority from U.S. Provisional Patent Application Ser. No. 60/829,978, filed on Oct. 18, 2006. The subject matter of the aforementioned applications is hereby incorporated by reference in their entireties.

TECHNICAL FIELD

The present invention relates generally to an apparatus for delivering a therapeutic agent into ocular tissue, and more particularly to an electrode assembly and related system for delivering at least one therapeutic agent into an ocular tissue of a subject.

BACKGROUND OF THE INVENTION

The treatment of ocular diseases in mammals, including humans and non-humans alike often requires that drugs or other agents be delivered to the eye in a therapeutic dose. Such diseases may occur in the choroid, the retina, the crystalline lens, and the optic nerve, as well as other ocular structures. One treatment methodology is to deliver an ocular agent to these structures via local drug administration, as opposed to systemic drug administration. This permits agents to be delivered directly to a site requiring evaluation and/or therapy. Because of drug localization, there is less of a concern for release or dissemination of the drug beyond the site of delivery. Such is also the case for other body sites where it is desirable to limit drug dissemination or systemic administration, yet still provide drugs in various formulations.

In many instances, however, local drug administration to the eye is not easily accomplished. Thus, localized drug administration often requires rather invasive procedures to gain access to the various ocular structures being treated. This may entail inserting a conduit, such as a fine gauge needle into the eye, or forming an incision for positioning of a device, such as a drug depot. Consequently, such treatment typically requires a visit to a hospital or doctor's office where trained health care professionals can perform the necessary, relatively more invasive procedures to achieve local drug administration.

SUMMARY OF THE INVENTION

According to one aspect of the present invention, a contact electrode assembly is provided for delivering at least one therapeutic agent into ocular tissue of a subject. The contact electrode assembly comprises a flexible dielectric layer, a first electrode portion, and a second electrode portion. The flexible dielectric layer includes oppositely disposed first and second surfaces. The first electrode portion is disposed on the first surface of the dielectric layer. The second electrode portion is disposed on a portion of the second surface of the dielectric layer. The second electrode portion comprises an interdigitated electrode that includes a first comb-shaped portion defining a first plurality of fingers and a second comb-shaped portion defining a second plurality of fingers. Each of the first electrode portion, the first comb-shaped portion, and the second comb-shaped portion is electrically connectable to a signal source.

According to another aspect of the present invention, a system is provided for motivating at least one therapeutic agent through an ocular membrane of a subject. The system comprises a cover electrode member, a contact electrode assembly in electrical communication with the cover electrode member, and a medicament layer. The cover electrode member has oppositely disposed first and second surfaces. The second surface includes an electrically-conductive portion that is electrically connectable to a signal source. The contact electrode assembly comprises a dielectric layer, a first electrode portion, and a second electrode portion. The dielectric layer includes oppositely disposed first and second surfaces. The second electrode portion is disposed on the first surface of the dielectric layer. The medicament layer includes the at least one therapeutic agent, and is disposed on a first major surface of the second electrode portion. The third electrode portion is disposed on a portion of the second surface of the dielectric layer. The third electrode portion comprises an interdigitated electrode that includes a first comb-shaped portion that defines a first plurality of fingers and a second comb-shaped portion that defines a second plurality of fingers. Each of the first electrode portion, the second electrode portion, the first comb-shaped portion, and the second comb-shaped portion is electrically connectable to a signal source.

According to another aspect of the present invention, a system is provided for motivating at least one therapeutic agent through an ocular membrane of a subject. The system comprises a dome-shaped cover electrode member, a dome-shaped contact electrode assembly in electrical communication with the cover electrode member, and a medicament layer. The cover electrode member has oppositely disposed first and second surfaces. The second surface includes an electrically-conductive portion that is electrically connectable to a signal source. The electrically-conductive portion comprises an electrically-conductive ink. The contact electrode assembly comprises a dielectric layer, a first electrode portion, and a second electrode portion. The dielectric layer includes oppositely disposed first and second surfaces. The second electrode portion is disposed on the first surface of the dielectric layer. The second electrode portion is comprised of an electrically-conductive ink. The medicament layer includes the at least one therapeutic agent, and is disposed on a first major surface of the second electrode portion. The third electrode portion is disposed on a portion of the second surface of the dielectric layer. The third electrode portion comprises an electrically-conductive ink. The third electrode portion comprises an interdigitated electrode that includes a first comb-shaped portion that defines a first plurality of fingers and a second comb-shaped portion that defines a second plurality of fingers. Each of the first electrode portion, the second electrode portion, the first comb-shaped portion, and the second comb-shaped portion is electrically connectable to a signal source.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1A is an exploded perspective view of a contact electrode assembly constructed in accordance with one aspect of the present invention;

FIG. 1B is an assembled perspective view of the contact electrode assembly in FIG. 1A;

DETAILED DESCRIPTION

Figure 2A:
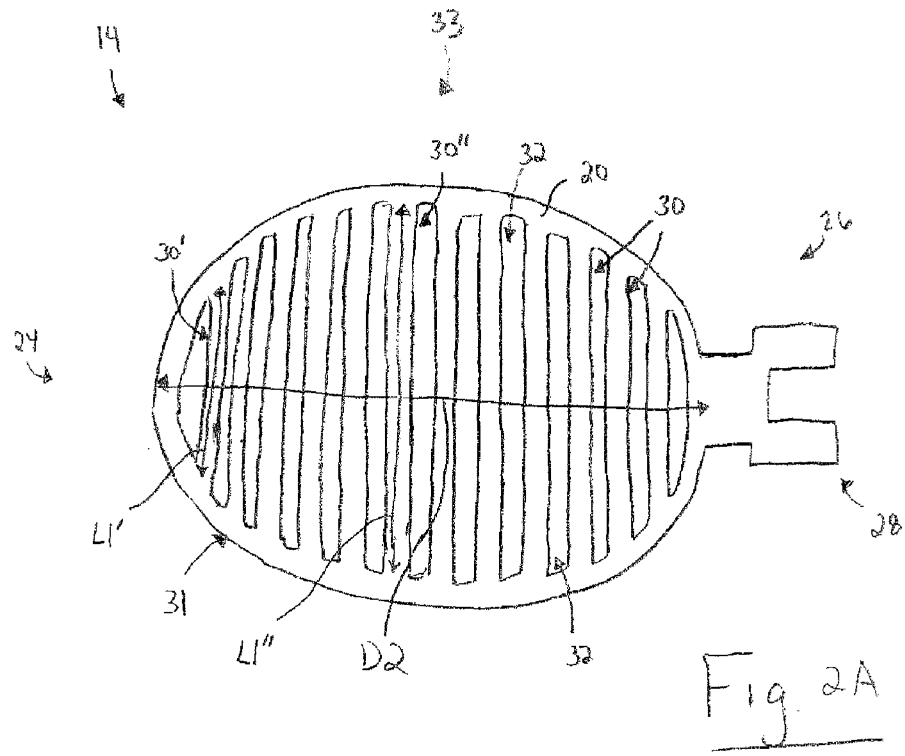
FIG. 2A is a top plan view of a dielectric layer comprising the contact electrode assembly in FIGS. 1A-B.

Unless otherwise defined, all technical terms used herein have the same meaning as commonly understood by one of ordinary skill in the art to which the present invention pertains.

In the context of the present invention, the term "ocular tissue" can refer to any one or combination of the tissues comprising the eye, such as the sclera, the conjunctiva, the cornea, the eyelid, tissues within the sclera (e.g., the retina) and outside the sclera (e.g., ocular muscles within the orbit), and tissues neurologically connected to (but distinct from) the eye, such as the optic nerve, the geniculate nucleus, and the visual cortex.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "therapeutic agent", "drug", "agent", "chemical compound", and "chemical substance" can refer to any polar or non-polar molecule or moiety that is capable of exhibiting a dipole moment when exposed to an electric field. The terms can include, but are not limited to, therapeutically effective agents (i.e., agents that are capable of having a biological effect), such as pharmaceutical agents, drugs, or biological agents.

As used herein, the term "medicament layer" can refer to a suitable reservoir for storing and releasing at least one therapeutic agent, either with or without a vehicle.

As used herein, the term "vehicle" can refer to any non-toxic carrier composition suitable for administration of a drug or agent into ocular tissue. Examples of vehicles can include any of the standard pharmaceutical carriers, such as a phosphate buffered saline solution, water, emulsions (e.g., oil/water emulsions), various types of wetting agents, and excipients.

As used herein, the term "signal" can refer to voltage signals and current signals.

As used herein, the term "therapeutically effective amount" can refer to that amount of a therapeutic agent that results in amelioration of symptoms or a prolongation of survival in a subject with an ocular disease or condition. A therapeutically effective amount relieves to some extent one or more symptoms of an ocular disease or condition or returns to normal either partially or completely one or more physiological or biochemical parameters associated with or causative of the ocular disease or condition.

As used herein, the term "electrical communication" can mean that certain parts or components of the present invention are in communication with each other by flow of electrons sufficient to generate an electric field therebetween.

The present invention relates generally to an apparatus for delivering a therapeutic agent into ocular tissue, and more particularly to an electrode assembly and related system for delivering at least one therapeutic agent into an ocular tissue of a subject. As representative of one aspect of the present invention, FIGS. 1A-B illustrate a contact electrode assembly 10 for delivering at least one therapeutic agent to an ocular tissue (not shown) of a subject. The present invention provides a non-invasive contact electrode assembly 10 and system 12 (FIGS. 6A-B) that take advantage of the principles of electrokinetic transport to modulate delivery of at least one therapeutic agent into ocular tissue. Unlike conventional therapeutic agent delivery modalities, the present invention provides increased patient safety, the ability to deliver both polar and non-polar agents of varying size, programmable dose control, and potentially lower cost of subject care.

One aspect of the present invention includes a contact electrode assembly 10 (FIGS. 1A-B) for delivering at least one therapeutic agent into an ocular tissue of a subject via dielectrophoresis. Briefly, dielectrophoresis involves providing a non-uniform alternating (AC) or direct (DC) electric field to a compound or agent. The non-uniform electric field, in addition to inducing a dipole in the compound or agent, sets up an electrical field gradient that provides an electromotive force on the newly polarized compound or agent, the magnitude and direction of which are dependent on several factors. A more detailed explanation of dielectrophoresis and its operating principles are disclosed in U.S. patent application Ser. No. 11/874,859 (hereinafter, "the '859 application"), the entirety of which is hereby incorporated by reference.

Referring to FIGS. 1A-B, the contact electrode assembly 10 comprises a dielectric layer 14, a first electrode portion 16, and a second electrode portion 18. The contact electrode assembly 10 has a generally dome-shaped configuration adapted to conform to the contour of ocular tissue when placed thereon. More particularly, the components of the contact electrode assembly 10 can have a radius of curvature that is identical or substantially similar to the radius of curvature of the ocular tissue (e.g., the sclera or cornea). The contact electrode assembly 10 has a diameter D1 that corresponds to, or is about equal to, the diameter of the ocular tissue surface upon which the contact electrode assembly is contacted. In one example of the present invention, the diameter D1 can be about 24 mm. It will be appreciated that the dimensions of the contact electrode assembly 10, such as the diameter D1 can be varied depending upon the particular anatomy of the ocular tissue and the subject's eye. The contact electrode assembly 10 can be formed by various coating and laser cutting techniques, such as printing (e.g., flexographic, rotogravure, inkjet, etc.) or lamination.

Figure 2B:
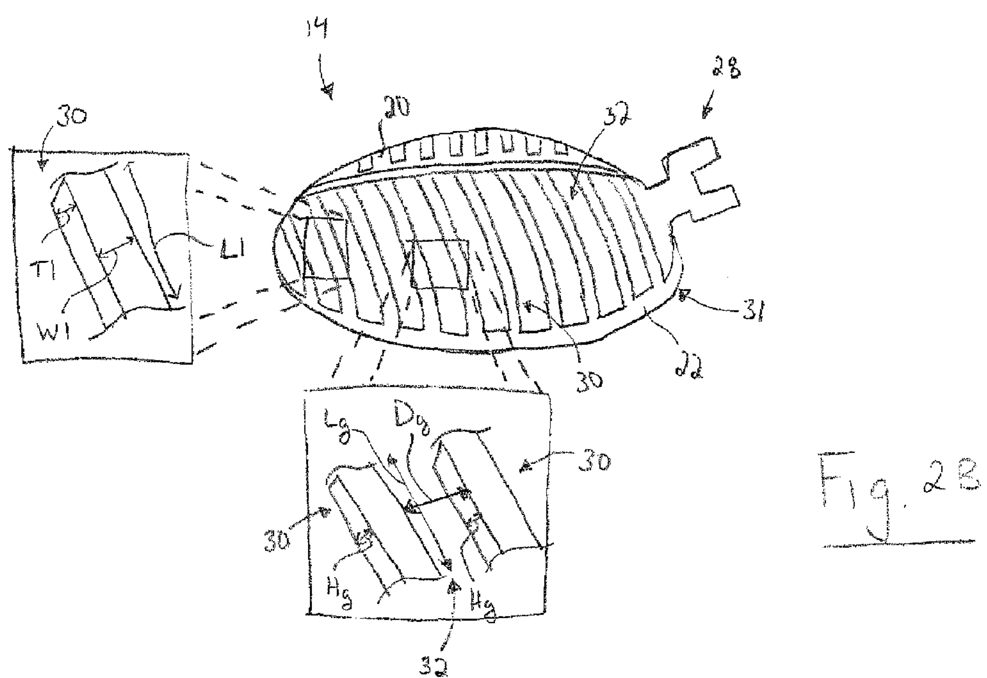
FIG. 2B is a perspective view taken from the bottom of the dielectric layer in FIG. 2A.

The dielectric layer 14 (FIGS. 2A-B) has a flexible configuration and is made from one or more electrically-insulative materials, such as polyester, silicon, and/or polypropylene. In one example of the present invention, the dielectric layer 14 is made of polyester. The dielectric layer 14 has a generally dome-shaped configuration and is defined by oppositely disposed first and second surfaces 20 and 22. One or both of the first and second surfaces 20 and 22 can be etched to facilitate adherence of an electrically-conductive ink thereto, as well as edge registration. The dielectric layer 14 also includes oppositely disposed first and seconds ends 24 and 26 that define a diameter D2. The diameter D2 can be equal to or approximately equal to the diameter D1 of the contact electrode assembly 10. For example, the diameter D2 can be about 24 mm. Alternatively, the diameter D2 can be greater than about 24 mm. The second end 26 of the dielectric layer 14 includes a tail-like extension tab 28 for supporting electrical leads or contacts (not shown). Although the extension tab 28 is shown as having a generally Y-shaped configuration, it will be appreciated that any other configuration may be used so long as one or more electrical leads or contacts can be supported thereon.

The process used to prepare the dielectric layer 14 (e.g., laser cutting) yields a dielectric layer comprising a plurality of rib members 30 spaced apart by a plurality of gaps 32 and integrally formed with a peripheral edge 31. As shown in one of the magnified window of FIG. 2B, each of the rib members 30 is defined by a length L1, a width W1, and a thickness T1. The length L1 of each of the rib members 30 varies between the first and second ends 24 and 26 of the dielectric layer 14. Generally, the length L1' of a rib member 30' located at the first end 24 is less than the length L1" of a different rib member 30" located in a center portion 33 of the dielectric layer 14. For example, the rib member 30' can have a length L1" of about 0.1 inch to about 0.3 inches (e.g., about 0.244 inches), and the rib member 30" can have a length L1" of about 0.4 inches to about 0.8 inches (e.g., about 0.689 inches).

The width W1 of each of the rib members 30 can be between about 0.002 inches and about 0.006 inches. In one example of the present invention, the width W1 of each of the rib members 30 is about 0.004 inches. The thickness T1 of each of the rib members 30 can be about 0.0005 inches to about 0.005 inches and, for example, about 0.002 inches. It will be appreciated that the length L1 of each of the rib members 30 will vary depending upon the anatomy of the subject's eye. Additionally, it will be appreciated that the dielectric layer 14 can include more or less than the number of rib members 30 shown in FIGS. 2A-B.

Each of the gaps 32 is formed between two rib members 30 and defined by a distance $D_g$, a height $H_g$, and a length $L_g$. Each of the gaps 32 extends between the first and second surfaces 20 and 22 of the dielectric layer 14. The dimensions of each of the gaps 32 are sufficient to allow an amount of at least one therapeutic agent to pass therethrough. The distance $D_g$ can be between about 0.002 inches and about 0.006 inches (e.g., about 0.002 inches). The distance $D_g$ between each of the gaps 32 can be the same or uniform throughout the dielectric layer 14. The height $H_g$ of each of the gaps 32 is equal to or about equal to the thickness T1 of the rib members 30. The length $L_g$ of each of the gaps 32 is equal to or about equal to the length L1 of each of the rib members 30. In other words, the length $L_g$ of each of the gaps 32 varies with the length L1 of each of the rib members 30 per the curvature of the dielectric layer 14.

The first electrode portion 16 (FIGS. 3A-B) is formed from an electrically-conductive material, such as electrically-conductive ink or conductive polymer(s). In one example of the present invention, the first electrode portion 16 is formed from an electrically-conductive ink containing a plurality of nano-silver particles that form a contiguous layer of conductive silver (e.g., upon heating) and, advantageously, exhibit a very low void percentage. It will be appreciated that other types of conductive particles, such as gold or platinum may be used as part of the electrically-conductive ink so long as the particular conductive particle(s) is/are generally hypoallergenic.

Figure 3A:
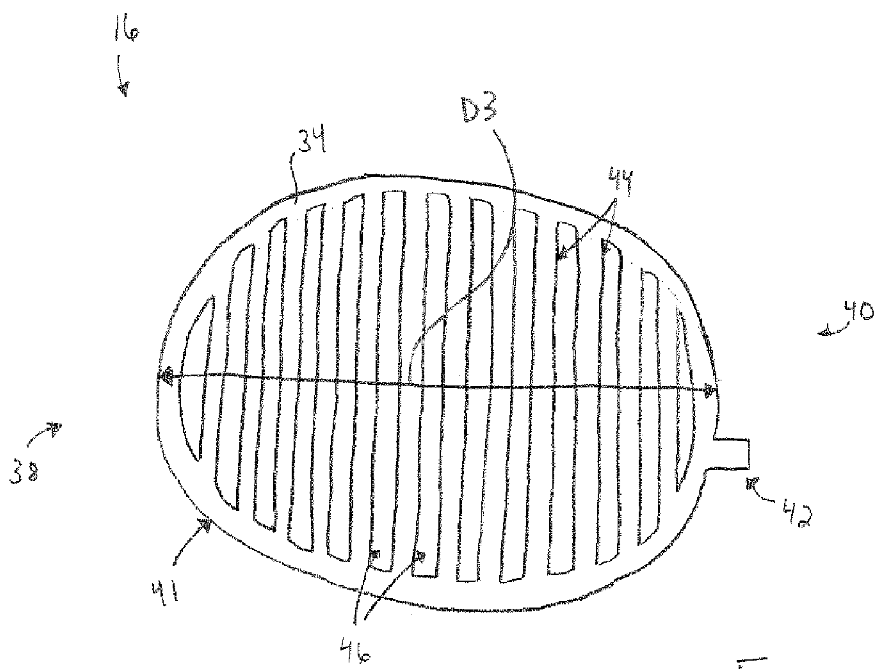
FIG. 3A is a top plan view of a first electrode portion of the contact electrode assembly in FIGS. 1A-B.
Figure 3B:
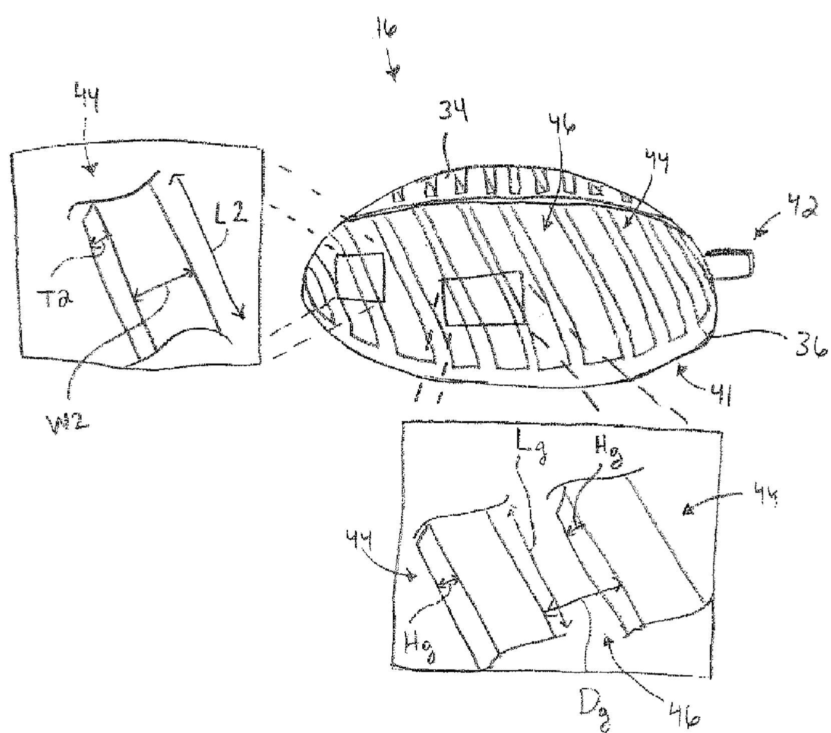
FIG. 3B is a perspective view taken from the bottom of the first electrode portion in FIG. 3A.

As shown in FIGS. 3A-B, the first electrode portion 16 has a dome-shaped configuration and is defined by oppositely disposed first and second surfaces 34 and 36, as well as by oppositely disposed first and second ends 38 and 40 that define a diameter D3. The diameter D3 can be equal to or approximately equal to the diameter D1 of the contact electrode assembly 10. For example, the diameter D3 can be about 24 mm. The second surface 36 is disposed on the first surface 20 of the dielectric layer 14 (FIG. 5B) using a coating and cutting process (e.g., laser cutting). For example, the first electrode portion 16 can comprise an electrically-conductive ink that is printed on the first surface 20 of the dielectric layer 14 (e.g., using flexographic printing). The electrically-conductive material used to form the first electrode portion 16 is continuously disposed on the first surface 20 of the dielectric layer 14 so that there are no gaps or breaks therein.

The second end 40 (FIGS. 3A-B) of the first electrode portion 16 includes at least one connecting portion or member 42 for electrically connecting the first electrode portion to a signal source (not shown) that is capable of providing an AC signal, a DC signal, or a combination thereof. The connecting portion or member 42 is positioned slightly off center as shown in FIG. 3A with respect to the diameter D3; however, it will be appreciated that the connecting portion or member can be centered about the first electrode portion 16. The connecting portion or member 42 can be comprised of the same electrically-conductive material used to form the first electrode portion 16 and can be continuous therewith.

The process (e.g., ink printing and laser cutting) used to form the first electrode portion 16 yields a plurality of rib members 44 spaced apart by a plurality of gaps 46 and integrally formed with a peripheral edge 41. The gaps 46 of the first electrode portion 16 are in fluid communication with the gaps 32 of the dielectric layer 14. As shown in one of the magnified windows in FIG. 3B, each of the rib members 44 is defined by a length L2, a width W2, and a thickness T2. The length L2 and the width W2 of each of the rib members 44 is equal to (or about equal to) the length L1 and width W1 of the rib members 30 comprising the dielectric layer 14. The thickness T2 of each of the rib members 44 can be about 1 micron to about 3 microns (e.g., about 1.2 microns). Additionally, dimensions of the gaps 46 comprising the first electrode portion 16 are equal to (or about equal to) the dimensions of the gaps 32 comprising the dielectric layer 14.

Figure 4A:
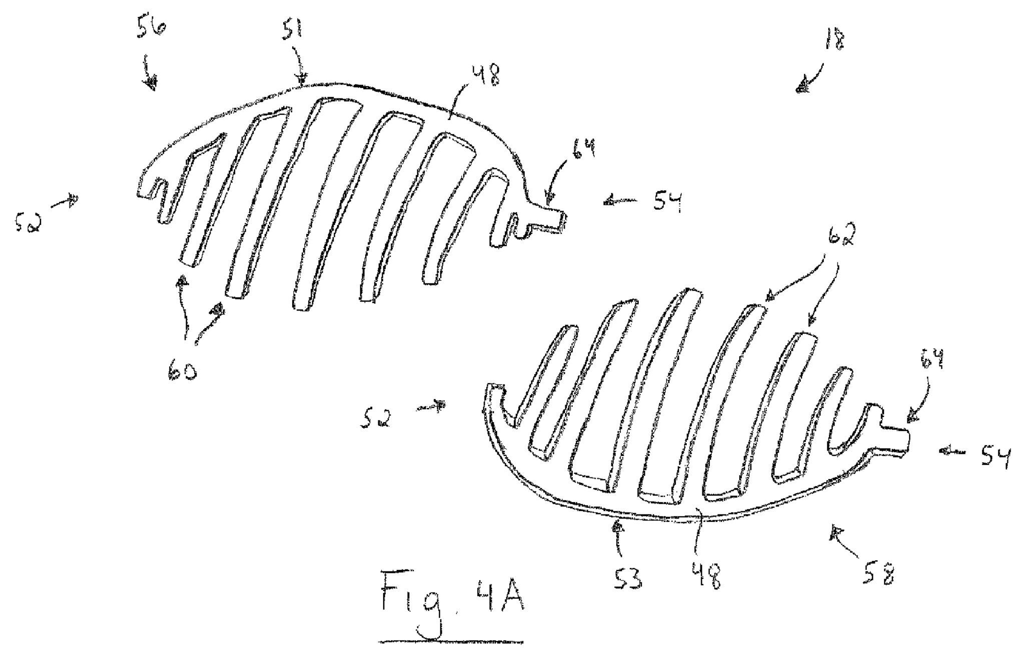
FIG. 4A is an exploded perspective view of a second electrode portion comprising the contact electrode assembly in FIGS. 1A-B.
Figure 4B:
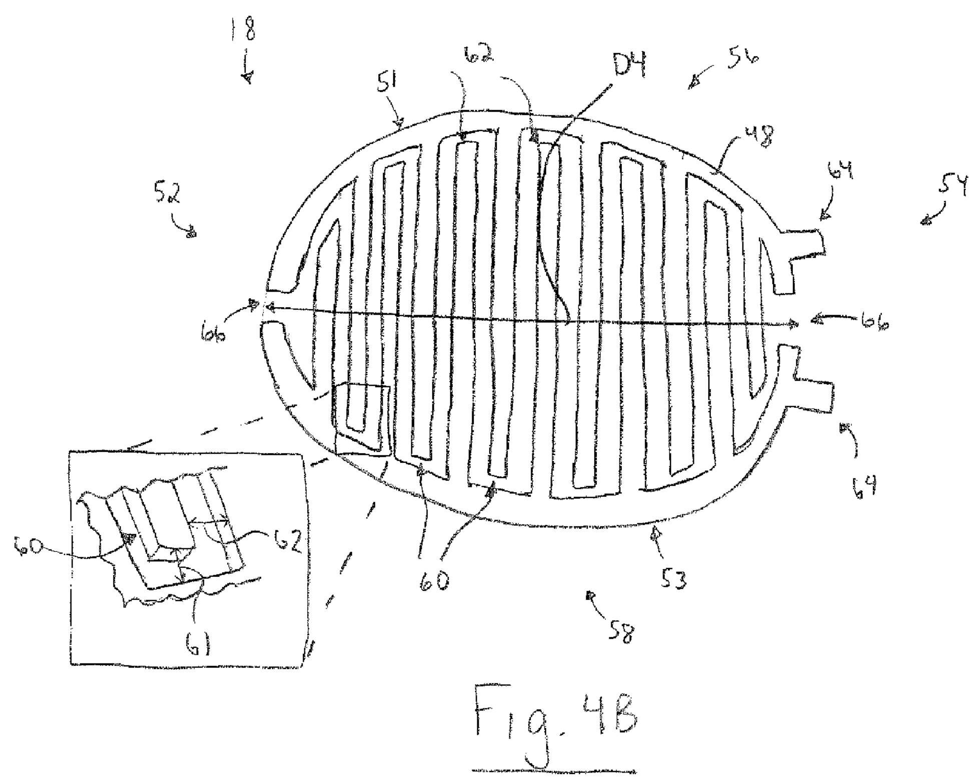
FIG. 4B is a top plan view of the second electrode portion in FIG. 4A.
Figure 4C:
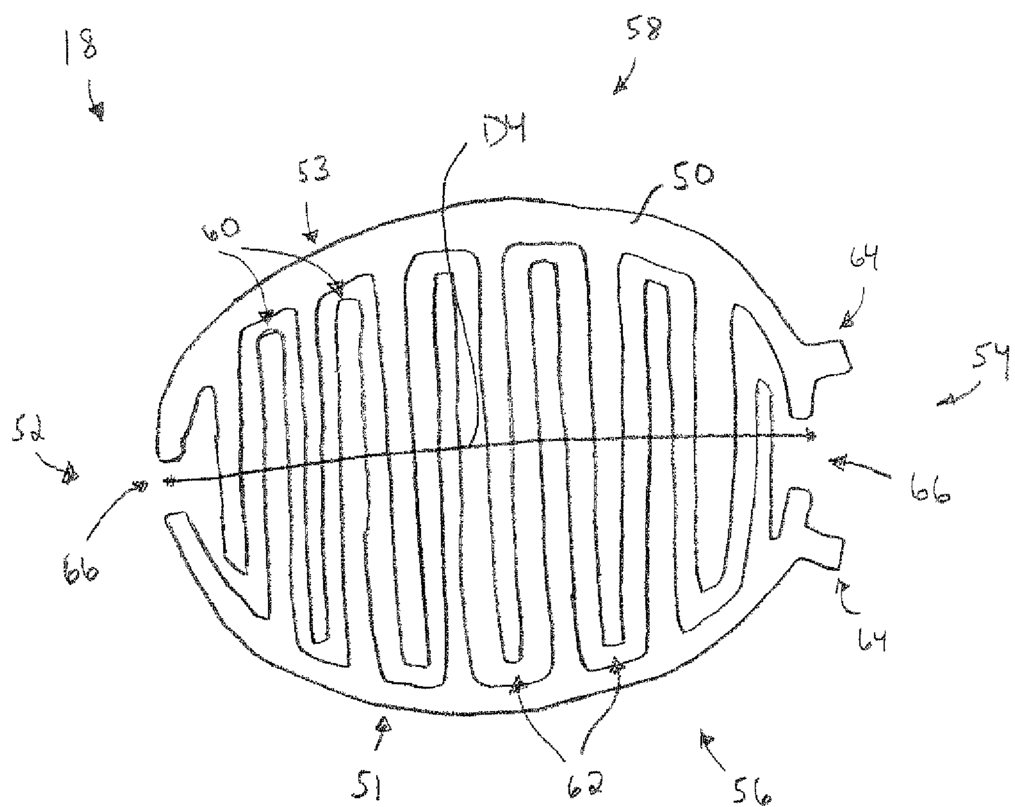
FIG. 4C is a bottom plan view of the second electrode portion in FIG. 4A.

Referring to FIGS. 4A-C, the second electrode portion 18 includes oppositely disposed first and second surfaces 48 and 50, as well as first and second ends 52 and 54 that define a diameter D4. The second electrode portion 18 has a flexible, dome-shaped configuration that is contoured to the three-dimensional shape of the ocular tissue (e.g., the eye). As shown in FIG. 5B, the first surface 48 of the second electrode portion 18 is disposed on a portion of the second surface 22 of the dielectric layer 14. The second electrode portion 18 (FIGS. 4A-C) is formed from an electrically-conductive material, such as electrically-conductive ink or conductive polymer(s). In one example of the present invention, the second electrode portion 18 is formed from an electrically-conductive ink containing a plurality of nano-silver particles that form a contiguous layer of conductive silver (e.g., upon heating). It will be appreciated that other types of conductive particles, such as gold or platinum may be used as part of an electrically-conductive ink so long as the particular conductive particle(s) is/are generally hypoallergenic.

The second electrode portion 18 comprises an interdigitated electrode formed from first and second comb-shaped portions 56 and 58. In general, an interdigitated electrode can include any set of at least two electrodes that contain interwoven projections. Each of the first and second comb-shaped portions 56 and 58 defines a first and second plurality of fingers 60 and 62, respectively, which are interleaved with one another and connected at (e.g., integrally formed with) one end to first and second peripheral edges 51 and 53. The second end 54 of each of the first and second comb-shaped portions 56 and 58 includes a connecting portion or member 64 for electrically connecting the first electrode portion to a signal source capable of providing an AC signal, a DC signal, or a combination thereof. The connecting portion or member 64 can be comprised of the same electrically-conductive material used to form the second electrode portion 18 and can be continuous therewith.

As shown in FIG. 4B, a series of gaps G1 and G2 extend vertically between the first and second surfaces 48 and 50 of the second electrode portion 18, and horizontally between the first and second fingers 60 and 62. The dimensions of the gaps G1 and G2 are uniform throughout the second electrode portion. Additionally, the dimensions of the gaps G1 and G2 are equal to (or about equal to) the dimensions of the gaps 46 comprising the first electrode portion 16 and the gaps 32 comprising the dielectric layer 14. The gaps G2 are in fluid communication with the gaps 46 extending through the first electrode portion 16 and the gaps 32 extending through the dielectric layer 14. Consequently, the gaps G2 comprising the second electrode portion 18, the gaps 46 comprising the first electrode portion 16, and the gaps 32 comprising the dielectric layer 14 form a series of channels that extend between the first surface 34 of the first electrode portion and the second surface 50 of the second electrode portion 18 to allow an amount of at least one therapeutic agent to pass therethrough.

Generally speaking, the width of the gaps 32, 46, and G2 dictates the electric field strength (i.e., drug driving force) for a given voltage and current. In other words, a narrower gap width results in a greater electric field strength (and vice-versa). Accordingly, it will be appreciated, for example, that the width of the gaps 32, 46, and G2 can be prepared (e.g., laser cut) in a particular pattern such that the width of the gaps corresponding to the eye lens is greater than the width of the surrounding gaps, thereby decreasing drug flow into that area of the eye and delivering more effective dosage of the drugs into the pars plana. Moreover, it will be appreciated that the configuration of one or all of the components forming the contact electrode assembly 10 can be engineered so that therapeutic agents are delivered to select portions of the eye during operation of the present invention. For example, the pattern of rib members 30 and 44, as well as the fingers 60 and 62 can be engineered to selectively deliver therapeutic agents to the pars plana by preparing a contact electrode assembly 10 without rib members 30 and 44 and fingers 60 and 62 that extending across a center portion thereof (i.e., imparting the contact electrode assembly with a ring-like structure).

Figure 5A:
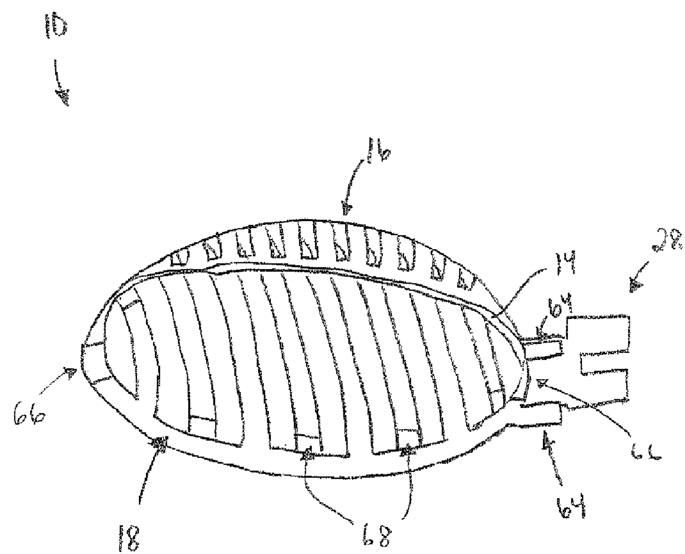
FIG. 5A is a perspective view taken from the bottom of the contact electrode assembly in FIG. 1B.
Figure 5B:
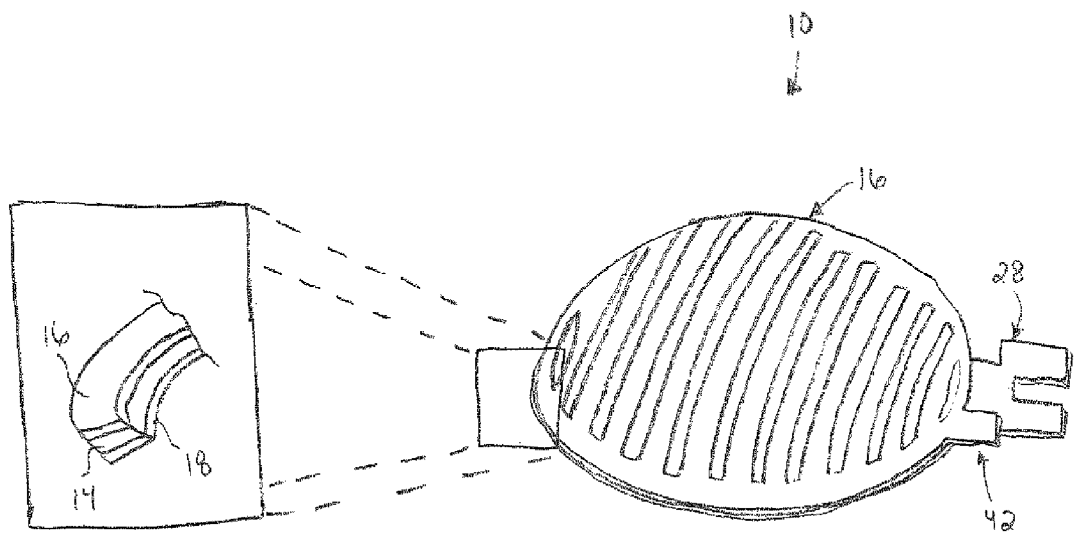
FIG. 5B is a perspective view taken from the top of the contact electrode assembly shown in FIG. 1B.

Referring to FIGS. 5A-B, the second electrode portion 18 is disposed upon the second surface 22 of the dielectric layer 14 so that centrally-aligned gaps 66 are formed at the first and second ends 52 and 54 of each of the first and second comb-shaped portions 56 and 58, respectively, thereby exposing a portion of the dielectric layer 14 at each of the central gaps. As can be seen in FIG. 5A, the interleaved pattern of the first and second fingers 60 and 62 that form the second electrode portion 18 also results in a series of peripheral gaps 68, which comprise exposed portions of the dielectric layer 14. Although not shown in FIGS. 1A-5B, it will be appreciated that the contact electrode assembly 10 can additionally or optionally include a layer or film to prevent or mitigate damage to the ocular tissue during placement and operation of the contact electrode assembly on the ocular tissue. For example, all or only a portion of the second surface 50 of the second electrode portion 18 can include a hydrogel to prevent or mitigate damage to the ocular tissue.

Figure 6A:
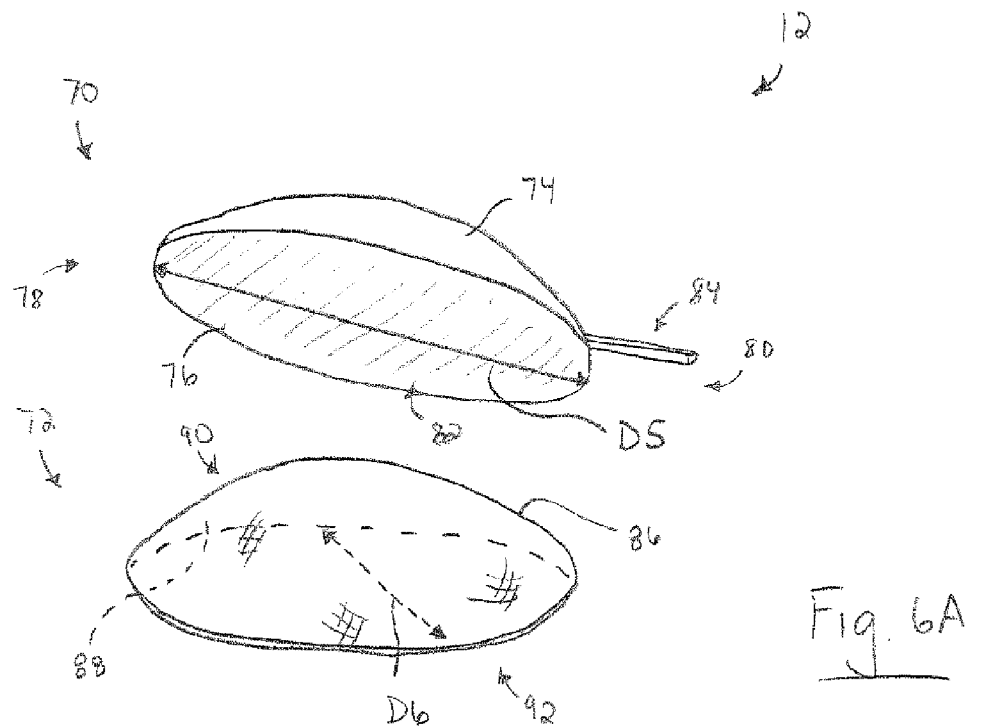
FIG. 6A is an exploded view of a system for motivating at least one therapeutic agent through an ocular membrane constructed in accordance with another aspect of the present invention.
Figure 6B:
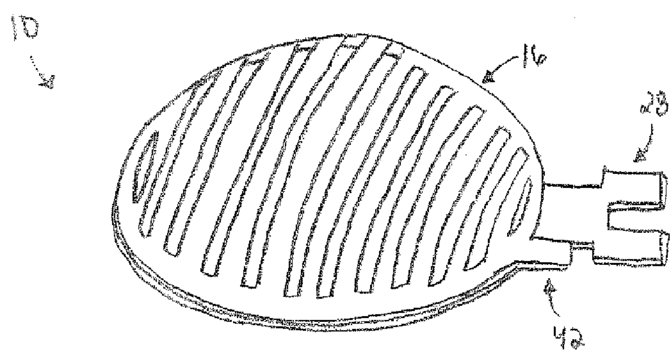
FIG. 6B is an assembled perspective view of the system in FIG. 6A.
Figure 6B:
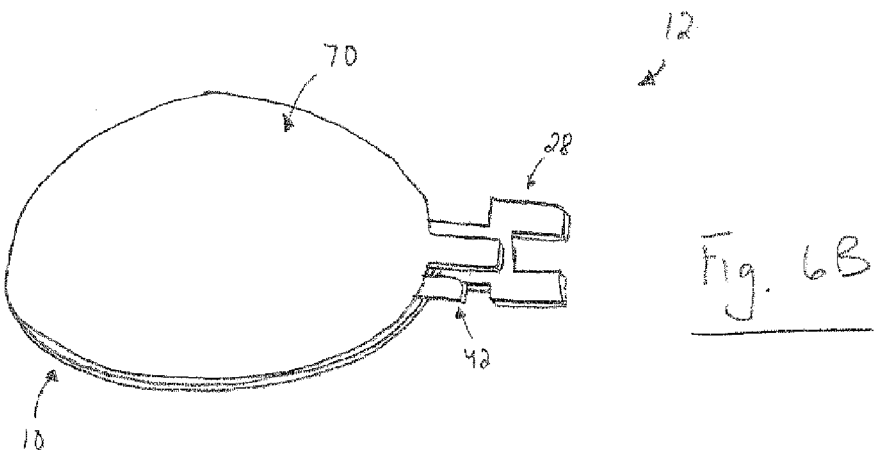

Another aspect of the present invention is illustrated in FIGS. 6A-B and includes a system 12 for motivating at least one therapeutic agent through an ocular membrane of a subject. The system 12 comprises a cover electrode member 70, a contact electrode assembly 10 in electrical communication with the cover electrode member, and a medicament layer 72 sandwiched between the cover electrode member and the contact electrode assembly. The contact electrode assembly 10 comprising the system 12 can be similar or identical to the contact electrode assembly described above and shown in FIGS. 1A-5B. The contact electrode assembly 10 and the cover electrode member 70 can be placed into electrical communication with one another by a variety of mechanisms, including a housing (not shown) that hingedly connects the contact electrode assembly with the cover electrode member. Alternatively, the contact electrode assembly 10 and the cover electrode member 70 can be placed into electrical communication with one another by the hand(s) of a user (e.g., a physician).

As shown in FIG. 6A, the cover electrode member 70 has a dome-shaped configuration and includes oppositely disposed first and second surfaces 74 and 76, as well as first and second ends 78 and 80 that define a diameter D5. The diameter D5 of the cover electrode member 70 can be equal to (or about equal to) the diameter D1 of the contact electrode assembly 10. For example, the diameter D5 can be about 24 mm. Each of the first and second surfaces 74 and 76 has a radius of curvature that equal to or about equal to the radius of curvature of the ocular tissue. The cover electrode member 70 is formed from an electrically-insulative material, such as polyester. At least a portion of the second surface 76 of the cover electrode member 70 includes an electrically-conductive material, which forms an electrically-conductive portion 82. For example, all or only a portion of the second surface 76 can include an electrically-conductive ink that is printed or laminated thereon. The electrically-conductive portion 82 is fluidly connected, and in electrical communication with, a connecting portion or member 84 for electrically connecting the electrically-conductive portion to a signal source capable of providing an AC signal, a DC signal, or a combination thereof. The connecting portion or member 84 can be comprised of the same electrically-conductive material used to form the electrically-conductive portion 82 and can be continuous therewith.

The medicament layer 72 has a dome-shaped configuration and includes oppositely disposed first and second surfaces 86 and 88, as well as first and second ends 90 and 92 that define a diameter D6. The diameter D6 of the cover electrode member 70 can be equal to (or about equal to) the diameter D1 of the contact electrode assembly 10. For example, the diameter D6 can be about 24 mm. Each of the first and second surfaces 86 and 88 has a radius of curvature that equal to (or about equal to) the radius of curvature of the ocular tissue. Although the medicament layer 72 is shown in FIG. 6A as being dome-shaped, it will be appreciated that the medicament layer can alternatively be shaped to preferentially deliver the at least one therapeutic agent to a select region of ocular tissue. For example, a ring-shaped medicament layer (not shown) can facilitate selective delivery of at least one therapeutic agent to the sclera of the eye while also avoiding or mitigating delivery of the at least one therapeutic agent to the cornea. It will thus be appreciated that the medicament layer 72 can have any size and shape, depending upon the particular application of the present invention.

The medicament layer 72 can comprise a matrix formed from a sponge, gel (e.g., hydro-gel), viscous liquid, or the like. The medicament layer 72 can be disposed on the first surface 34 of the first electrode portion 16 when the system 12 is assembled as shown in FIG. 6B. The medicament layer 72 can be disposed on the first surface 34 by spraying, coating or placing. The material(s) used to form the medicament layer 72 can include any one or combination of materials capable of storing and releasing the at least one therapeutic agent and, optionally, at least one vehicle. For example, the medicament layer 72 can be comprised of a biocompatible, non-biodegradable polymeric material made from a homopolymer, a copolymer, straight polymers, branched polymers, cross-linked polymers, stimuli-responsive polymers, or a combination thereof. Examples of such polymers can include silicone, polyvinyl alcohol, ethylene vinyl acetate, polylactic acid, nylon, polypropylene, polycarbonate, cellulose, cellulose acetate, polyglycolic acid, polylactic-glycolic acid, cellulose esters, polyethersulfone, acrylics, their derivatives, and combinations thereof. It should be appreciated that the medicament layer 72 may also be disposed on the first surface 34 of the first electrode portion 16 or at least partially embedded therein.

The medicament layer 72 can include any one or combination of polar and/or non-polar therapeutic agents. For example, the medicament layer 72 can include such ophthalmic medications as anti-infectives, antibiotics, anti-inflammatory agents (e.g., triamcinolone), non-steroidal anti-inflammatory agents, anti-fungal agents, glaucoma medications (e.g., alpha-2 agonists, beta blockers, carbonic anhydrase inhibitors, miotics, prostaglandin agonists, and sympathomimetics), mast cell stabilizers, anti-proliferative agents, steroids, corticosteroids, hormones, small molecules, cytokines, growth factors, antibodies or antibody fragments, immune system modulators, vectors, polynucleotides, nucleic acids, RNAs, miRNAs, siRNAs, DNAs, aptamers, carbohydrates, recombinant or native peptides, polypeptides and proteins (e.g., TIMP-3), enzymes, enzyme inhibitors, and combinations thereof. More specific examples of such therapeutic agents, as well as others are known in the art.

It will be appreciated that the system 12 can include more than one medicament layer 72, and that each medicament layer can contain the same or different type of therapeutic agent. Additionally, it will be appreciated that a single medicament layer 72 can include two or more compartments (not shown), each of which is also made from a gel, viscous liquid, etc. If appropriate, mixtures of therapeutic agents can be stored in a common compartment while other single therapeutic agents (or mixtures) are stored in one or more separate compartments. The release characteristics of the respective compartments can be adjusted according to specific applications of the present invention.

Operation of the system 12 to motivate at least one therapeutic agent through an ocular membrane can proceed as follows. The system 12 can be assembled as shown in FIG. 6B. The particular dimensions of the system 12, as well as the type of therapeutic agent(s) comprising the medicament layer 72 will depend on the subject's anatomy, the age of the subject, the presence or absence of an ocular condition or disease, as well as other factors. To treat retinal inflammation, for example, the medicament layer 72 can include a desired concentration of triamcinolone. Alternatively, in a subject with advanced macular degeneration, the medicament layer 72 can include a desired concentration of ranibizumab or TIMP-3. The connecting portions or members 84, 42, and 64 of each of the cover electrode member 70 and the contact electrode assembly 10 can be electrically connected to the same or different signal source (e.g., an AC signal source).

Next, an electrical signal having certain characteristics is delivered to the electrically-conductive portion 82 of the cover electrode member 70 so that the electrically-conductive portion obtains a first polarity. For example, an AC signal can have an orienting frequency of about 0.1 Hz to about 100 Hz, a motivating frequency of between about 100 Hz and about 20,000 Hz, and an amplitude of between about 1 V to about 10 V. A more specific description of the electrical signal used to modulate the electrical signal is disclosed in the '859 application. An electrical signal having the same or similar characteristics is then provided to the first electrode portion 16 of the contact electrode assembly 10 so that the first electrode portion obtains a second polarity that is opposite the first polarity. Charging of the electrically-conductive portion 82 and the first electrode portion 16 is referred to as the "orientation mode" of the system 12, which creates an orientation charge between the electrically-conductive portion and the first electrode portion, thereby inducing a dipole on the therapeutic agents and orienting the therapeutic agents in a vertical alignment between the two charged surfaces.

Once orientation mode is complete, the electrical signals are discontinued to the electrically-conductive portion 82 and the first electrode portion 16. An electrical signal having certain characteristics is then supplied to the second electrode portion 18 of the contact electrode assembly 10, which is referred to as the "delivery mode". More particularly, the delivery mode includes delivering opposite first and second electrical signals to the first and second comb-shaped portions 56 and 58 of the second electrode portion 18. Doing so creates an electric field loop at each gap G1 and G2 between the oppositely-charged series of first and second fingers 60 and 62 comprising the second electrode portion 18. The generated electric field forms above the first surface 48 of the second electrode portion 18 (i.e., in the medicament layer 72) and continues downward below the second surface 50 of the second electrode portion into the ocular tissue. Consequently, the therapeutic agents are motivated through the ocular membrane without mechanically disrupting the ocular membrane.

It will be appreciated that the system of the present invention can be used to deliver a therapeutically effective amount of the at least one therapeutic agent to ocular tissue and thereby treat a variety of ocular diseases or conditions, such as macular edema, age-related macular degeneration, anterior, intermediate and posterior uveitis, HSV retinitis, diabetic retinopathy, bacterial, fungal or viral endophthalmitis, eye cancers, glioblastomas, glaucoma, glaucomatous degradation of the optic nerve, and combinations thereof.

From the above description of the invention, those skilled in the art will perceive improvements, changes and modifications. Although the present invention is described in terms of providing a contact electrode assembly 10 and related system 12 for delivering at least one therapeutic agent via dielectrophoresis, it will be appreciate that the present invention can facilitate delivery of therapeutic agents via other electrokinetic transport mechanisms, such as electrophoresis and iontophoresis. Such improvements, changes, and modifications are within the skill of the art and are intended to be covered by the appended claims.

Having described the invention, we claim:

1. A system for motivating at least one therapeutic agent through an ocular membrane of a subject, said system comprising:

a cover electrode member having oppositely first and second surfaces, said second surface including an electrically-conductive portion that is electrically connectable to a signal source;

a contact electrode assembly in electrical communication with said cover electrode member, said contact electrode assembly comprising:

a flexible dielectric layer having oppositely disposed first and second surfaces;

a second electrode portion disposed on said first surface of said dielectric layer;

a third electrode portion disposed on a portion of said second surface of said dielectric layer, said third electrode portion comprising an interdigitated electrode that includes:

a first comb-shaped portion defining a first plurality of fingers; and a second comb-shaped portion defining a second plurality of fingers; and a medicament layer including the at least one therapeutic agent, said medicament layer being disposed on a first surface of said second electrode portion;

wherein each of said first electrode portion, said second electrode portion, said first comb-shaped portion, and said second comb-shaped portion is electrically connectable to a signal source.

2. The system of claim 1, wherein said second electrode portion comprises a plurality of ribs spaced apart from one another by a first plurality of gaps sufficient to allow an amount of the at least one therapeutic agent to pass therethrough.

3. The system of claim 1, wherein each of said first, second, and third electrode portions is dome-shaped and adapted to conform to the contour of the ocular tissue when said system is contacted with the ocular membrane.

4. The system of claim 1, wherein each of said first and second pluralities of fingers is spaced apart by a second plurality of gaps sufficient to allow an amount of the at least one therapeutic agent to pass therethrough.

5. The system of claim 1, wherein the signal source is an AC signal source capable of providing an electric signal having an orienting frequency or an electrical signal having a motivating frequency, or both.

6. The system of claim 1, wherein the ocular membrane is not mechanically disrupted by the system.

7. The system of claim 1, wherein each of said first, second, and third electrode portions is comprised of an electrically-conductive ink.

8. The system of claim 7, wherein each of said second and third electrode portions is printed onto said first and second surfaces of said dielectric layer, respectively.

9. A system for motivating at least one therapeutic agent through an ocular membrane of a subject, said system comprising:

a dome-shaped cover electrode member having oppositely first and second surfaces, said second surface including an electrically-conductive portion that is electrically connectable to a signal source, said electrically-conductive portion comprising an electrically-conductive ink;

a dome-shaped contact electrode assembly in electrical communication with said cover electrode member, said contact electrode assembly comprising:

a flexible, dome-shaped dielectric layer having oppositely disposed first and second surfaces;

a second electrode portion disposed on said first surface of said dielectric layer, said second electrode portion comprising an electrically-conductive ink;

a dome-shaped third electrode portion disposed on a portion of said second surface of said dielectric layer, said third electrode portion comprising an electrically-conductive ink, said third electrode portion comprising an interdigitated electrode that includes:

a first comb-shaped portion defining a first plurality of fingers; and a second comb-shaped portion defining a second plurality of fingers; and a medicament layer including the at least one therapeutic agent, said medicament layer being disposed on a first surface of said second electrode portion;

wherein each of said first electrode portion, said second electrode portion, said first comb-shaped portion, and said second comb-shaped portion is electrically connectable to a signal source.

10. The system of claim 9, wherein the ocular membrane is not mechanically disrupted by the system.

* * * * *